United States Patent
Grodzki et al.

(10) Patent No.: US 9,934,357 B2
(45) Date of Patent: Apr. 3, 2018

(54) PROTOCOL ADJUSTMENT FOR MEDICAL IMAGING

(71) Applicants: David Grodzki, Erlangen (DE); Björn Heismann, Erlangen (DE)

(72) Inventors: David Grodzki, Erlangen (DE); Björn Heismann, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 47 days.

(21) Appl. No.: 14/936,785

(22) Filed: Nov. 10, 2015

(65) Prior Publication Data

US 2016/0140293 A1  May 19, 2016

(30) Foreign Application Priority Data

Nov. 14, 2014  (DE) .................. 10 2014 223 293

(51) Int. Cl.
  *G06K 9/00*  (2006.01)
  *G06F 19/00*  (2018.01)

(52) U.S. Cl.
  CPC .................. *G06F 19/321* (2013.01)

(58) Field of Classification Search
  CPC ..................................... G06F 19/321
  See application file for complete search history.

(56) References Cited

U.S. PATENT DOCUMENTS

| | | | |
|---|---|---|---|
| 2002/0029157 A1* | 3/2002 | Marchosky | G06F 19/322 |
| | | | 705/3 |
| 2004/0082845 A1 | 4/2004 | Matsumoto et al. | |
| 2006/0058658 A1 | 3/2006 | King et al. | |
| 2007/0118243 A1* | 5/2007 | Schroeder | A61B 17/8061 |
| | | | 700/118 |
| 2008/0103834 A1 | 5/2008 | Reiner | |
| 2008/0243759 A1* | 10/2008 | Martin | A61B 5/055 |
| 2010/0135543 A1 | 6/2010 | Weese et al. | |
| 2011/0153255 A1 | 6/2011 | Horger et al. | |
| 2012/0008846 A1* | 1/2012 | Meetz | A61B 6/032 |
| | | | 382/131 |

(Continued)

FOREIGN PATENT DOCUMENTS

| | | |
|---|---|---|
| CN | 1765328 A | 5/2006 |
| CN | 101116110 A | 1/2008 |
| DE | 102009054990 A1 | 6/2011 |

OTHER PUBLICATIONS

German Office action for related German Application No. 10 2014 223 293.7, dated Apr. 7, 2015, with English Translation.

(Continued)

*Primary Examiner* — Oneal R Mistry
(74) *Attorney, Agent, or Firm* — Lempia Summerfield Katz LLC

(57) ABSTRACT

A method and a device for protocol adjustment for medical imaging, and a medical imaging device and a computer program product for carrying out the method, wherein the method includes providing a location-specific feature of an imaging device, ascertaining at least one location-dependent protocol boundary condition from a comparison with at least one database, and creating at least one protocol adjusted to the at least one location-dependent protocol boundary condition. At least one of the providing, ascertaining, or creating occurs automatically.

17 Claims, 3 Drawing Sheets

(56) References Cited

U.S. PATENT DOCUMENTS

| | | | | |
|---|---|---|---|---|
| 2013/0304512 A1* | 11/2013 | Seshadri | ............... | G06F 19/322 |
| | | | | 705/3 |
| 2015/0039336 A1* | 2/2015 | Mayer | .................. | A61B 5/0059 |
| | | | | 705/2 |
| 2015/0078522 A1* | 3/2015 | Makino | .................. | A61B 6/563 |
| | | | | 378/62 |
| 2016/0012182 A1* | 1/2016 | Golay | ................... | G06F 19/321 |
| | | | | 705/3 |

OTHER PUBLICATIONS

Chinese Office Action for related Chinese Application No. 201510761731.2 dated Nov. 23, 2017, with English Translation.

* cited by examiner

PROTOCOL ADJUSTMENT FOR MEDICAL IMAGING

This application claims the benefit of DE 10 2014 223 293.7, filed on Nov. 14, 2014, which is hereby incorporated by reference in its entirety.

TECHNICAL FIELD

The embodiments relate to a method and to a device for protocol adjustment for medical imaging, and to a medical imaging device and to a computer program product for carrying out the method.

BACKGROUND

Imaging methods are important aids in medical technology. Therefore, in clinical cross-sectional imaging for instance, magnetic resonance tomography (MRT) is characterized by high and variable soft tissue contrasts. A wide variety of contrasts, such as T1, T2, or susceptibility weighting may be adjusted as a function of measuring parameters, such as echo time, repetition time, pre-pulses, and sequence types. In addition, inter alia field of view (FoV), resolution, and slice thickness may be adjusted. However, even with other modalities certain adjustment values, such as tube current and tube voltage in computer tomography (CT), influence the quality of the resulting images. The complete set of parameter adjustments is called a (measuring) protocol.

Conventionally, the treating physician may not choose the parameters completely freely and instead, the physician adheres to certain boundary conditions that are specified by local authorities (such as the Medical Association in Germany) to be able to bill a health insurance fund for the creation of images. These procedures may vary greatly depending on location and also differ for example within a federal state or administrative district. The situation may also occur where different contrasts are demanded for specific problems in region A than in region B.

Following installation of a new imaging device the protocols are therefore conventionally adjusted to the local regulations before the start of regular patient treatment. In many cases, the protocols are adjusted such that the specifications are still just adhered to in the case of minimum measuring time. In addition, the situation may occur where different preferences of the treating physicians even within one medical facility, (e.g., a hospital), have to be taken into account.

This procedure of the initial adjustment of the protocols has previously been carried out on each individual device by an application specialist, e.g., in the case of MRT devices. The time required for this may extend to several days or even weeks, so high costs may accrue as a result. Furthermore, such an adjustment of the protocols may not always be carried out, in particular, in emerging and developing countries due to a lack of specialists. If an adjustment of this kind is omitted, this may potentially lead to a poor image quality and/or the image recordings may not be billed.

SUMMARY AND DESCRIPTION

The scope of the present invention is defined solely by the appended claims and is not affected to any degree by the statements within this summary. The present embodiments may obviate one or more of the drawbacks or limitations in the related art.

It is the object of the present embodiments to disclose a method and a device for adjusting at least one protocol for medical imaging that enables at least partially automated protocol creation.

A method for adjusting at least one protocol for medical imaging therefore includes the following acts: a) providing a location-specific feature of an imaging device, b) ascertaining at least one location-dependent protocol boundary condition from a comparison with at least one database, and c) creating at least one protocol adjusted to the at least one location-dependent protocol boundary condition. At least one of the acts a) to c) occurs automatically.

Imaging methods in which protocols, which may be designed in particular as protocol trees, may be used are radiography, computed tomography (CT), mammography, magnetic resonance tomography (MRT), positron emission tomography (PET), single photon emission computed tomography (SPECT), scintigraphy, sonography, thermography, and electrical impedance tomography (EIT). By way of simplification MRT-specific properties will primarily be discussed in the following statements.

Providing the location-specific feature of an imaging device may include active ascertainment of the device location, (for example, by a local device), which is installed at the site of the imaging device. The location-specific feature may therefore be the ascertained physical location of the device itself.

The location-specific feature may also be allocated to a location in a non-local manner, however, for example, by transferring it to a different location, (in particular, by remote data transmission), and being allocated to a device location at this other location. In this case, the feature would not be the device location itself but a different feature that is capable of ascertaining the location of the device. For example, a serial number of the device may therefore be used if an allocation table exists between serial number and device location.

Use for example of a device-specific link, (e.g., a hyperlink), therefore constitutes provision of a location-specific feature. A database having at least one location-dependent protocol boundary condition may therefore then be held in readiness at the address of the hyperlink by way of any allocation table, which may potentially be stored with the manufacturer of the imaging device. The contents of the database may be retrieved with the aid of the hyperlink by remote data transmission.

Using the location-specific feature, the at least one database is advantageously queried for at least one protocol boundary condition that applies to this location. This at least one boundary condition may be a complete location-specific protocol itself that is taken over potentially unchanged from the at least one database in order to produce the protocol. At least one protocol may therefore be uniquely manually created by taking into account specified parameters and be stored in the at least one database, so it may be used for any imaging device that is located in a certain region.

This at least one boundary condition may also be a direct stipulation within the protocol to be created, for example in which region a specific protocol parameter is allowed to lie. This at least one boundary condition may also be a specification from which at least one parameter of the protocol to be created may be derived, for example, by a calculation formula. Possible protocol boundary conditions influence, for example, specifications on the size of the field of view or resolution.

The protocol may be created by automatic protocol conversion by, for example, modifying a specified standard protocol data record. Any specifications may be integrated, existing values (such as resolution) adjusted and effects on other parameters, which are not expressly specified (such as echo time), calculated and finally the at least one protocol created.

The advantages of the present embodiments lie in a more effective, (e.g., faster and less expensive), provision of the protocols, which do not have to be carried out for each imaging device individually, in particular in situ, by an application specialist. In addition, the risk that image recordings are carried out with adjustments that may conflict with the applicable settlement rules may be reduced.

In an advantageous embodiment, the location of the imaging device is ascertained in act a) as a location-specific feature by a location-determining unit.

A location-determining unit of this kind may ascertain the location, for example, by a GPS sensor and forward this information to another unit, (in particular, the evaluation unit). Other localization methods such as via an IP address, WLAN data, or other methods familiar to a person skilled in the art, as may also be used, for example, in the locating of mobile phones and/or smartphones, are also conceivable.

A location-determining unit may simplify working processes and contribute to automation of the image recording process. Furthermore, the risk of incorrect manual inputting of the location may be reduced.

In a further embodiment, the location is ascertained from a stored address. This variant is advantageous since ascertaining the location from a stored address may be carried out easily in technical terms. For example, additional hardware, such as a GPS sensor, may be dispensed with.

The address may be stored for instance in a DICOM header. DICOM stands for Digital Imaging and Communication in Medicine and is a standard for storing and exchanging information in medical image data management. It would also be conceivable for the address, (for example, a delivery address), to be stored in a central address list from which it may be retrieved by comparison with a possible identification feature, linked to the address, of the imaging device, in particular, a serial number.

At least one location-dependent protocol boundary condition of at least one location, (e.g., globally all locations), is advantageously stored in the at least one database. Depending on the respective boundary condition they may be allocated within the at least one database to a plurality of location groups including individual locations, (for example, countries). Precisely the taking into account of all globally possible locations may constitute an administrative simplification since it is thereby conceivable to map the at least one location-dependent protocol boundary condition in just one single central database.

At least one location-dependent protocol boundary condition, which results at least partially from specifications of at least one authority, may be stored in the at least one database. Boundary conditions for a protocol are in particular location-dependent since, depending on location, different authorities, such as agencies, offices, organizations, medical associations, and/or other authorities, determine specifications. Therefore billing principles in particular may constitute a location-dependent protocol boundary condition.

The at least one location-dependent protocol boundary condition then influences, for example, the adjustment of at least one device-specific measuring parameter. The congruence of this measuring parameter with applicable settlement rules may therefore be advantageously provided.

A further embodiment provides that the at least one database is at least partially locally stored at the site of the imaging device and/or is provided at least partially by remote transmission.

One possible variant, according to which the database is accessed purely locally, has the advantage that it operates independently of external devices. A local installation may, for example, occur as early as before delivery of the imaging device by the manufacturer. In this case, an infrastructure for remote data transmission, which potentially does not even exist at the site of the imaging device or would have to be installed at considerable costs, may therefore be dispensed with.

It is, moreover, conceivable for a remote transmission to occur automatically after the installation of the imaging device by way of a network, (in particular, the Internet), and to load the parameters required for the relevant location.

These parameters may be at least partially permanently stored locally after the loading process, so access to the parameters for creating the at least one protocol occurs locally and renewed establishment of contact with a central database by way of the network may be dispensed with. This is advantageous if a permanent connection is not desired, for example, for cost or security reasons. Furthermore, the availability of the imaging device is not limited, or is not greatly limited, thereby even in the event of failure of the network. This does not rule out contact subsequently being established temporarily again, for example for updates, by way of the network and data being loaded by remote transmission.

It is, however, also conceivable for the information required for creation of the protocol to only be stored in a non-local database and to be re-loaded with each protocol creation by remote transmission. An embodiment of this kind may potentially resort to technological methods as are known for cloud computing applications.

A non-local database may be centrally stored, so a plurality of imaging systems accesses the same database. It may also be decentralized, so access is made to a user-specific database. In both cases, the database may be made available and/or updated by a central station, for example, by a manufacturer of the imaging device.

It is also possible for some of the data required for creation of the protocol to be stored in a local sub-database and for some to be stored in a non-local sub-database.

A further variant of the method provides that at least one location-dependent protocol boundary condition is stored in the database that takes into account at least one patient insurance type. This may be information useful for the adjustment of the protocol since, for example, different billing conditions may apply to privately insured patients than to legally insured ones. Processes in a hospital for example may be simplified hereby.

A further embodiment includes an additional method act d) that provides adjustment of the protocol by a user. The protocol may therefore still be individually changed by way of a user interface even after potential automatic creation in order to optimize, for example, specific measuring parameters for the examination problem present in each case.

A user is in particular taken to refer to a person who operates the imaging device itself, (for example, a physician's assistant, a medical specialist, and/or a medical technical assistant). It may, however, also be a person who is not necessarily directly involved in the image recording process, such as for example a physician.

Moreover, in a further variant of the method at least one location-dependent protocol boundary condition, which includes at least one limitation, is stored in the at least one database. This limitation limits the adjustment of the protocol by the user in act d).

Specifications, which are mapped by the at least one location-dependent protocol boundary condition, are advantageously integrated directly in the adjustable limits of the corresponding protocols. If, for example, it is specified for an MRT image recording that a T1 knee measurement may have a maximum FoV of 250 mm, the limits are set such that even in the event of a change to other parameters by the user a FoV of 250 mm is not exceeded. This is primarily advantageous since physicians often also change the protocols later according to their preferences.

It is also conceivable for the possibilities of protocol adjustment to be configured differently according to groups of people that are to be defined. Therefore, one physician may be allowed more extensive possibilities for change, for example a greater number of changeable parameters, than a medical technical assistant for instance.

A further embodiment of the method provides that at least one location-dependent protocol boundary condition is stored in the at least one database, which takes into account the specifications of at least one user, (in particular, a treating physician). This variant increases the operating convenience of the method. It may, for example, be implemented in that, specific to the user, only protocols preferred by the user are displayed, for instance, in that a filter is placed over the proposed protocols.

A device for the adjustment of at least one protocol for medical imaging includes at least one database in which at least one location-dependent protocol boundary condition may be stored, and an evaluation unit that is connected to the at least one database. The evaluation unit is designed to receive the at least one location-dependent protocol boundary condition and to generate at least one protocol therefrom. The device is configured to carry out a method for the adjustment of at least one protocol for medical imaging.

The advantages of the device for the adjustment of at least one protocol for medical imaging substantially match the advantages of the method for the adjustment of at least one protocol for medical imaging that have been stated above in detail. Features, advantages, or alternative embodiments mentioned in this connection may likewise be transferred to the other claimed subject matters as well and vice versa.

The advantages of the device therefore lie in more effective, in particular, faster and less expensive, provision of the protocols that does not have to be carried out individually by an application specialist for each imaging device. In addition, the risk of image recordings being carried out with adjustments that conflict with the applicable settlement rules may be reduced.

The claimed device additionally includes in a further variant a location-determining unit and/or a user interface.

A user interface of this kind may be an operator terminal that includes a display unit, in particular a monitor, and an input unit, in particular a keyboard, a computer mouse and/or a microphone.

A medical imaging device includes an imaging device and a device.

A computer program product includes a program and may be loaded directly into a memory of a programmable evaluation unit of a device for adjusting at least one protocol for medical imaging. It includes a program to carry out a method when the program is run in the evaluation unit of the device for adjusting at least one protocol for medical imaging.

A further device includes a medical imaging device and a computer program product.

A potential data transfer unit may enable the necessary flow of data between the various cooperating units of the described devices. The data may potentially be transferred wirelessly and/or by cabling.

BRIEF DESCRIPTION OF THE DRAWINGS

Various exemplary embodiments will be described and illustrated in more detail below with reference to figures, in which.

DETAILED DESCRIPTION

Figure 1:
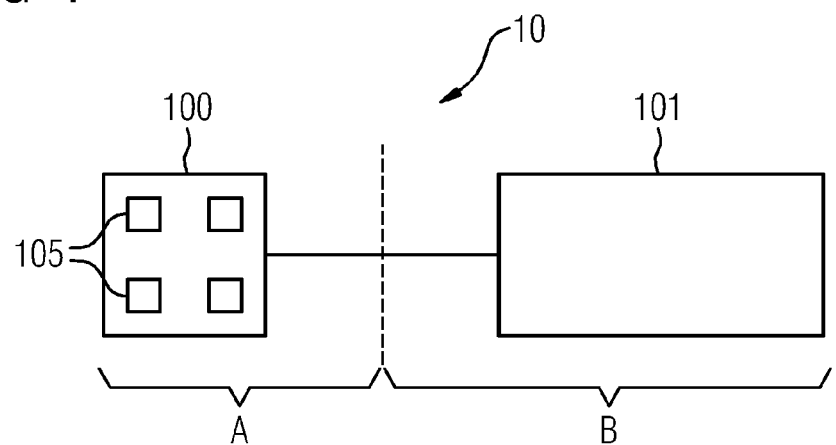
FIG. 1 depicts a schematic diagram of an example of a device.

FIG. 1 depicts a device 10 for the adjustment of at least one protocol for medical imaging.

The device 10 includes a database 100 in which at least one (in the illustrated example: four) location-dependent protocol boundary condition 105 is stored, and an evaluation unit 101 that is connected to the at least one (in the illustrated example: one) database 100. The evaluation unit 101 is capable of receiving the location-dependent protocol boundary conditions 105 and generating at least one protocol therefrom.

The database 100 is positioned in a region A. This may be physically separate from region B, for instance, an installation space in which the evaluation unit 101 is located. The database 100 may be located, for example, in a different room, a different building, a different town or a different country to the evaluation unit 101.

Figure 3:
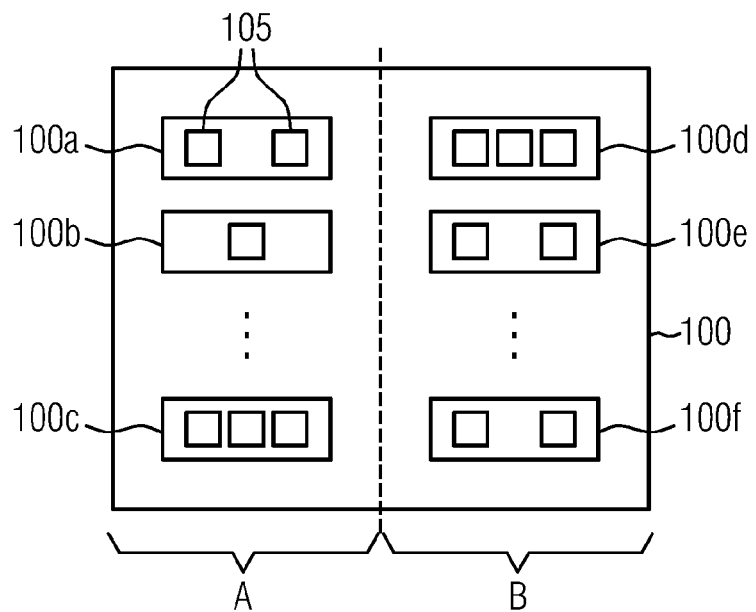
FIG. 3 depicts a schematic diagram of an example of one possible database structure.

It is also possible, as depicted in FIG. 3, for the database 100 to be physically divided into a plurality of sub-databases 100a to 100f that are partially located in region B in the immediate local vicinity of the evaluation unit 101 (100d, 100e and 100f), and partially physically separated further in region A (100a, 100b and 100c). In addition, it is conceivable for the database 100 to also be stored in a memory unit of the evaluation unit.

The data may be transferred between database and evaluation unit by a data transfer unit, possibly wirelessly and/or via cabling.

Figure 2:
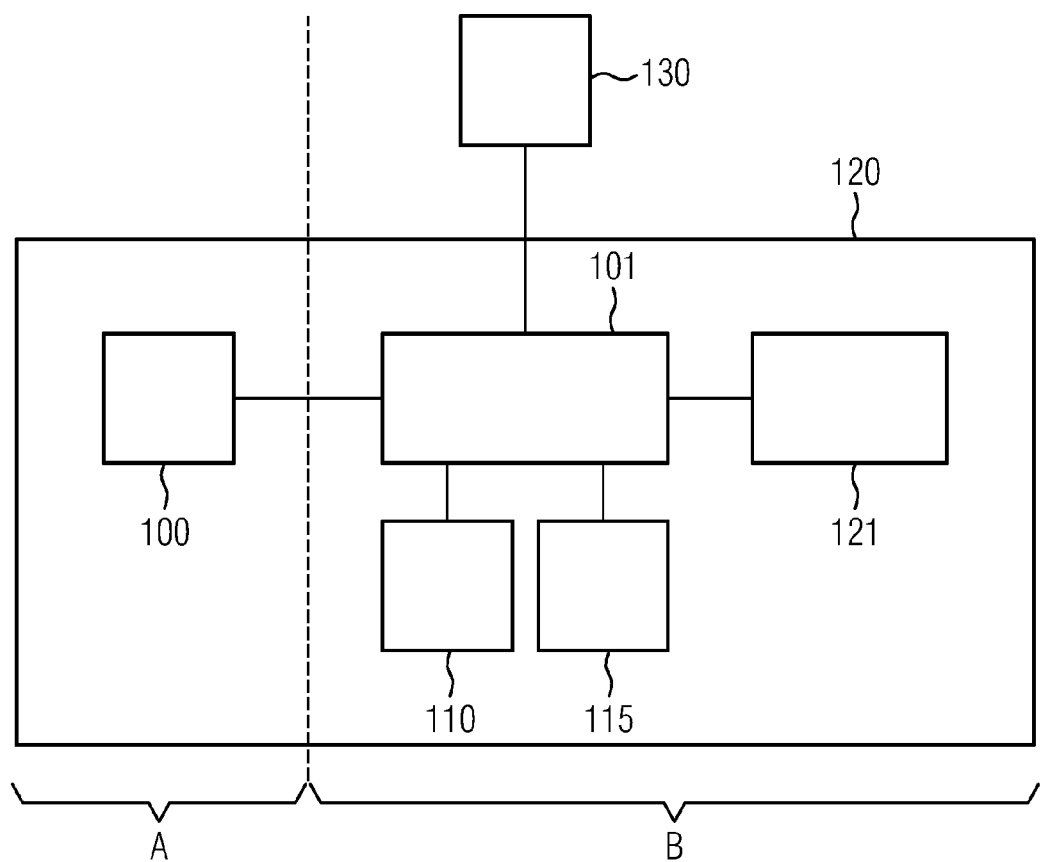
FIG. 2 depicts a schematic diagram of an example of an expanded form of the device that includes a plurality of variants.

FIG. 2 depicts an embodiment of a device for the adjustment of at least one protocol for medical imaging that is expanded in relation to FIG. 1. The following description is substantially limited to the differences from the exemplary embodiment in FIG. 1, with reference being made to the description of the exemplary embodiment in FIG. 1 in relation to components, features, and functions that are the same. Components, features, and functions that are substantially the same are basically numbered with the same reference numerals.

FIG. 2 firstly depicts an expanded embodiment of the device that also includes a location-determining unit 110. Location information may be fed to the evaluation unit 101 by this location-determining unit 110. The location-determining unit 110 may include, for example, a GPS unit or other devices as are used for localization for instance in mobile communications technology.

FIG. 2 also includes a variant of the device that additionally includes a user interface 115. This may enable a user to intervene manually in the at least one created protocol and to adjust it to his preferences.

As an expansion of the medical imaging device 120, an imaging device 121 is also incorporated. This may, in particular, be an X-ray machine, a computer tomograph, mammography device, magnetic resonance tomograph, positron emission tomograph, single-photon emission computer tomograph, scintigraphy device, ultrasound device, thermography device, or an electrical impedance tomograph.

FIG. 2 also depicts a computer program product 130. This includes a program and may be loaded directly into a memory of a programmable evaluation unit 101 of a device. The program provides that at least one of the methods, which are depicted in FIGS. 4 and 5, is carried out when the program is run in the evaluation unit 101.

As an alternative to the embodiment depicted in FIG. 2 the device may also include just one location-determining unit 110 and/or user interface 115 and/or imaging device 121 and/or computer program product 130.

Figure 4:
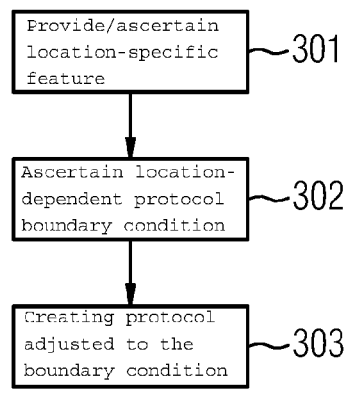
FIG. 4 depicts a flow chart of an embodiment of a method.
Figure 5:
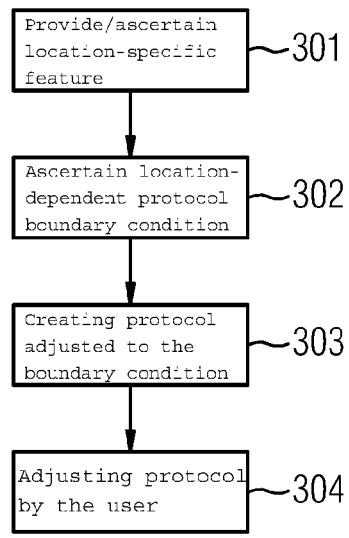
FIG. 5 depicts a flow chart of an alternative embodiment of the method.

According to the method depicted in FIG. 4 a location-specific feature of the imaging device is provided in act 301. This may occur for example by access of the evaluation unit 101 to a serial number stored in the device or by way of a manual input of the location, in particular by way of an input via a user interface 115.

Alternatively the location is advantageously ascertained in act 301 by a location-determining unit 110 that may in particular use a stored address. Since this location-determining process may be at least partially automated the risk of possible incorrect manual inputs is reduced.

Act 301 may be automatically and/or independently carried out by the evaluation unit 101 and/or location-determining unit 110.

In act 302, at least one location-dependent protocol boundary condition is ascertained from a comparison with at least one database 100. At least one location-dependent protocol boundary condition 105 of at least one location may be stored in the at least one database 100. This act may be implemented by the evaluation unit 101 searching through the database 100 for information that is relevant to the location.

This at least one protocol boundary condition 105, which is stored in the at least one database 101, conventionally results at least partially from specifications from an authority, such as, in particular, a medical association. This at least one protocol boundary condition 105 optionally takes account of at least one patient insurance type, moreover. This may advantageously ensure the billability of the medical examination that has been carried out.

The database 100 may be stored at least partially locally at the site of the imaging device and/or it is partially provided by remote transmission, as is described in FIGS. 1 and 2.

Act 302 may be carried out automatically and/or independently by the evaluation unit 101.

In a further act 303, at least one protocol is created by the evaluation unit 101 that is adjusted to the at least one location-dependent protocol boundary condition 105. This adjustment may include inter alia that measuring parameters, such as the resolution, are set such that they match any specifications from a medical association.

Act 303 may be carried out automatically and/or independently by the evaluation unit 101.

In a further variant of the method, it may be provided that at least one location-dependent protocol boundary condition 105 is stored in the at least one database 100, which takes into account specifications of at least one user, in particular, a treating physician. This consideration may find its expression in that a filter is placed over proposed protocols, so only the protocols that are preferred by him are displayed for a specific user.

FIG. 5 depicts an expanded method that includes an additional act 304 in which the protocol is adjusted by a user. This intervention by the user provides that the protocol may still be configured, for instance by the user interface 115, for the examination to be carried out, for example, to take into account specific characteristics of an examination object.

In an advantageous embodiment of the method, at least one limitation limits the adjustment of the protocol by the user. For this purpose, at least one location-dependent protocol boundary condition 105 is stored in the at least one database 100, and this includes this at least one limitation.

These limited processing possibilities of the protocol may prevent, for example, changed protocol parameters infringing one or more specification(s). It is conceivable, moreover, that when at least one protocol parameter is changed by the user, at least one further protocol parameter that is dependent thereon is automatically adjusted. This advantageously occurs such that given protocol boundary conditions 105 continue to be taken into account. This may prevent, for example, a change by the user unintentionally leading to a medical examination that may not be billed.

Figure 6:
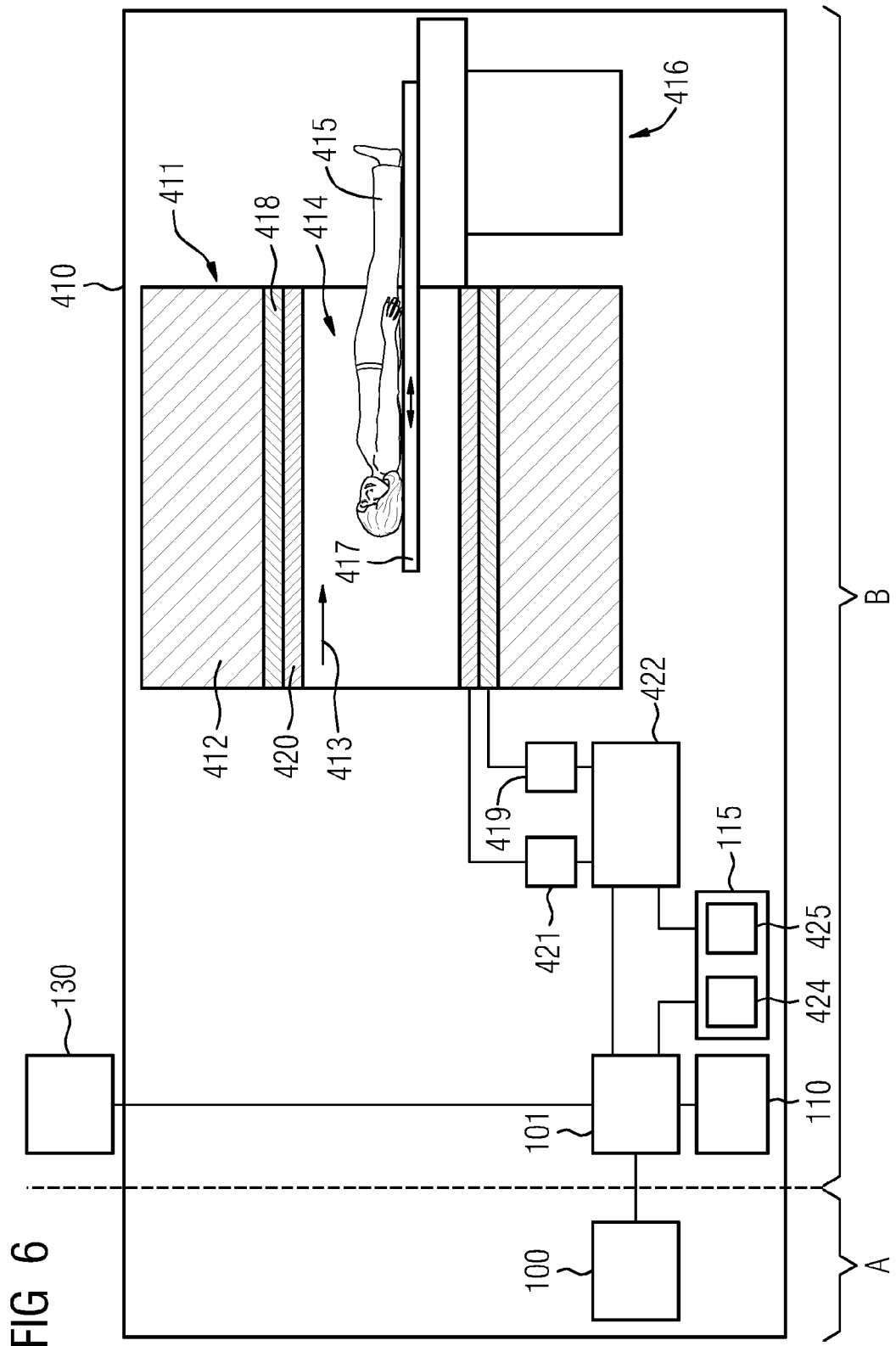
FIG. 6 depicts a schematic diagram of an example of a medical imaging device.

FIG. 6 schematically depicts as an example of a medical imaging device 120 a magnetic resonance device 410. It is also conceivable, however, for other imaging methods to be used.

The magnetic resonance device 410 includes a magnetic unit 411 including a superconductive main magnet 412 for generating a strong, and in particular constant, main magnetic field 413. The magnetic resonance device 410 also has a patient-receiving region 414 for receiving a patient 415. The patient-receiving region 414 in the present exemplary embodiment is cylindrical and cylindrically surrounded by the magnetic unit 411 in a circumferential direction. A different design of the patient-receiving region 414 is also conceivable. The patient 415 may be pushed by a patient-positioning device 416 of the magnetic resonance device 410 into the patient-receiving region 414. The patient-positioning device 416 has for this purpose an examination table 417 that may be moved inside the patient-receiving region 414.

The magnetic unit 411 also has a gradient coil unit 418 for generating magnetic field gradients that are used for spatial encoding during imaging. The gradient coil unit 418 is controlled by a gradient control unit 419 of the magnetic resonance device 410. The magnetic unit 411 also includes a high-frequency antenna unit 420 that in the present exemplary embodiment is designed as body coils permanently integrated in the magnetic resonance device 410. The high-frequency antenna unit 420 is designed to excite atomic nuclei that establish themselves in the main magnetic field 413 generated by the main magnet 41. The high-frequency antenna unit 420 is controlled by a high-frequency antenna control unit 421 of the magnetic resonance device 410 and emits high-frequency magnetic resonance sequences into an examination space that is substantially formed by a patient-receiving region 414 of the magnetic resonance device 410. The high-frequency antenna unit 420 is also designed to receive magnetic resonance signals.

The magnetic resonance device 410 has a system control unit 422 to control the main magnet 412, gradient control unit 419 and to control the high-frequency antenna control unit 421. The system control unit 422 centrally controls the magnetic resonance device 419, such as, for example, carrying out a predefined imaging gradient echo sequence. In addition, the system control unit 422 includes an evaluation unit for an evaluation of medical image data that is acquired during the magnetic resonance examination. The magnetic resonance device 410 also includes a user interface 115 that is connected to the system control unit 422. Control information, such as, for example, imaging parameters and reconstructed magnetic resonance images may be displayed on a display unit 424, (for example, on at least one monitor), of the user interface 115 for a medical operator. The user interface 115 also has an input unit 425 by which information and/or parameters may be input by the medical operator during a measuring process.

An evaluation unit 101 supplies protocol data to the system control unit 422 and this is processed further and implemented by the system control unit 422. The protocol data conventionally determines control signals that the system control unit 422 sends to the gradient control unit 419 and the high-frequency antenna control unit 421. To be able to generate the protocol data, the evaluation unit accesses the at least one database 100 in which at least one location-dependent protocol boundary condition 105 is stored. The database is in a region A that may be physically separate from region B. The at least one database 100 may be accessed for example via a remote data transfer via telephone line. A location-determining unit 110 may supply the evaluation unit 101 with location information that it uses to generate a location-specific protocol. A user may make individual protocol adjustments via the user interface 115.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for adjusting at least one protocol for medical imaging, the method comprising:
providing, by a location-determining unit, a physical location of an imaging device, wherein the imaging device is associated with a plurality of location-dependent protocol boundary conditions, each location-dependent protocol boundary condition relating to a particular physical location of the imaging device;
ascertaining at least one location-dependent protocol boundary condition of the plurality of location-dependent boundary conditions from a comparison of the provided physical location of the imaging device with at least one database, wherein the at least one database is (1) stored at least partially locally at the physical location of the imaging device, (2) provided at least partially by remote transmission, or (3) stored at least partially locally at the physical location of the imaging device and provided at least partially by remote transmission; and
creating at least one protocol adjusted to the at least one location-dependent protocol boundary condition,
wherein at least one of the providing, the ascertaining, or the creating occurs automatically.

2. The method as claimed in claim 1, further comprising:
ascertaining the physical location of the imaging device by a global positioning sensor (GPS) of the location-determining unit.

3. The method as claimed in claim 1, further comprising:
ascertaining the physical location from a stored address.

4. The method as claimed in claim 1, wherein the at least one location-dependent protocol boundary condition is stored in the at least one database.

5. The method as claimed in claim 1, wherein stored in the at least one database is the at least one location-dependent protocol boundary condition, which results at least partially from specifications of at least one authority.

6. The method as claimed in claim 1, wherein stored in the at least one database is at least one location-dependent protocol boundary condition that takes into account at least one patient insurance type.

7. The method as claimed in claim 1, wherein the protocol is adjusted by a user.

8. The method as claimed in claim 7, wherein stored in the at least one database is at least one location-dependent protocol boundary condition having at least one limitation, wherein the at least one limitation limits the adjustment of the protocol by the user.

9. The method as claimed in claim 1, wherein stored in the at least one database is at least one location-dependent protocol boundary condition that takes into account the specification of at least one user.

10. The method as claimed in claim 9, wherein the user is a treating physician.

11. A device for adjusting at least one protocol for medical imaging, the device comprising:
at least one database in which a plurality of location-dependent protocol boundary conditions is configured to be stored, wherein each location-dependent boundary condition relates to a particular physical location of an imaging device; and
an evaluation unit connected to the at least one database, wherein the evaluation unit is configured to receive the plurality of location-dependent protocol boundary conditions and generate at least one protocol therefrom,
wherein the device is configured to provide a physical location of an imaging device, ascertain at least one location-dependent protocol boundary condition of the plurality of location-dependent protocol boundary conditions from a comparison of the physical location of the imaging device with at least one database having the plurality of location-dependent boundary conditions, and create at least one protocol adjusted to the at least one location-dependent protocol boundary condition.

12. The device as claimed in claim 11, wherein the device comprises a location-determining unit.

13. The device as claimed in claim 12, wherein the device comprises a user interface.

14. The device as claimed in claim 11, wherein the device comprises a user interface.

15. A medical imaging device comprising:
an imaging device; and
a device for adjusting at least one protocol for medical imaging, the device comprising:
at least one database in which a plurality of location-dependent protocol boundary conditions is configured to be stored, wherein each location-dependent boundary condition relates to a particular physical location of an imaging device; and
an evaluation unit connected to the at least one database, wherein the evaluation unit is configured to receive the plurality of location-dependent protocol boundary conditions and generate at least one protocol therefrom,
wherein the device is configured to provide a physical location of an imaging device, ascertain at least one location-dependent protocol boundary condition of the plurality of location-dependent protocol boundary conditions from a comparison of the physical location of the imaging device with at least one database having the plurality of location-dependent boundary conditions, and create at least one protocol adjusted to the at least one location-dependent protocol boundary condition.

16. A device comprising:
a memory;
a computer program product having a program configured to be loaded directly into the memory of a programmable evaluation unit of the device for adjusting at least one protocol for medical imaging, wherein the program is run in the evaluation unit of the device for adjusting at least one protocol for medical imaging, the program configured to:
provide a physical location of an imaging device, wherein the imaging device is associated with a plurality of location-dependent protocol boundary conditions, each location-dependent protocol boundary condition relating to a particular physical location of the imaging device;
ascertaining at least one location-dependent protocol boundary condition of the plurality of location-dependent boundary conditions from a comparison of the provided physical location of the imaging device with at least one database; and
create at least one protocol adjusted to the at least one location-dependent protocol boundary condition.

17. A medical imaging device comprising:
an imaging device;
at least one database in which a plurality of location-dependent protocol boundary conditions is configured to be stored, wherein each location-dependent boundary condition relates to a particular physical location of an imaging device;
an evaluation unit connected to the at least one database, wherein the evaluation unit is configured to receive the plurality of location-dependent protocol boundary conditions and generate at least one protocol therefrom; and
a program evaluation unit having a computer program product comprising a program configured to be loaded directly into a memory of the programmable evaluation unit of the device, wherein the program is run in the evaluation unit of the device for generating the at least one protocol for the medical imaging,
wherein the medical imaging device, with the computer program product, is configured to: (1) provide a physical location of the imaging device, (2) ascertain at least one location-dependent protocol boundary condition of the plurality of location-dependent protocol boundary conditions from a comparison of the physical location of the imaging device with at least one database having the plurality of location-dependent boundary conditions, and (3) create at least one protocol adjusted to the at least one location-dependent protocol boundary condition.

* * * * *